(12) United States Patent
Ikku

(10) Patent No.: US 10,309,903 B2
(45) Date of Patent: Jun. 4, 2019

(54) ICP EMISSION SPECTROPHOTOMETER

(71) Applicant: Hitachi High-Tech Science Corporation, Minato-ku, Tokyo (JP)

(72) Inventor: Yutaka Ikku, Tokyo (JP)

(73) Assignee: Hitachi High-Tech Science Corporation, Minato-ku, Tokyo (JP)

( * ) Notice: Subject to any disclaimer, the term of this patent is extended or adjusted under 35 U.S.C. 154(b) by 0 days.

(21) Appl. No.: 15/926,097

(22) Filed: Mar. 20, 2018

(65) Prior Publication Data

US 2018/0275069 A1    Sep. 27, 2018

(30) Foreign Application Priority Data

Mar. 21, 2017    (JP) ................... 2017-054491

(51) Int. Cl.
| | |
|---|---|
| *G01J 3/30* | (2006.01) |
| *G01N 21/73* | (2006.01) |
| *G01J 3/443* | (2006.01) |
| *G01J 3/28* | (2006.01) |
| *G01J 3/18* | (2006.01) |
| *G01N 21/68* | (2006.01) |

(Continued)

(52) U.S. Cl.
CPC ............ *G01N 21/73* (2013.01); *G01J 3/0235* (2013.01); *G01J 3/04* (2013.01); *G01J 3/18* (2013.01); *G01J 3/2823* (2013.01); *G01J 3/443* (2013.01); *G01N 21/68* (2013.01); *G01J 2003/045* (2013.01)

(58) Field of Classification Search
CPC ......... G01N 21/73; G01N 21/68; G01J 3/443; H01J 49/105; H05H 1/30; G01B 11/24; G01B 11/2433; G01B 11/245; G01B 11/306; G02B 21/0016
USPC ...................................................... 356/316
See application file for complete search history.

(56) References Cited

U.S. PATENT DOCUMENTS

| | | | |
|---|---|---|---|
| 2007/0146688 A1* | 6/2007 | Tezuka ................. | G01J 9/02 356/124 |
| 2009/0195764 A1* | 8/2009 | Takenaka .............. | G03F 7/706 355/53 |

(Continued)

FOREIGN PATENT DOCUMENTS

| | | |
|---|---|---|
| JP | S63-063755 U | 4/1988 |
| JP | 2010-169412 A | 8/2010 |

*Primary Examiner* — Md M Rahman
(74) *Attorney, Agent, or Firm* — Banner & Witcoff, Ltd.

(57) ABSTRACT

An ICP emission spectrophotometer includes an inductively coupled plasma device, a spectroscope, and a computer. The spectroscope includes an incidence window, an incidence side slit, a diffraction grating, an emission window, an emission side slit, and a detector. Measurement conditions including diffraction condition and a measurement result are displayed on a display device. In a case where there are a plurality of diffraction conditions each including a combination of a diffraction grating and a diffraction order for measuring desired diffracted light, comparison information including at least an intensity and a resolution of emitted light in the diffraction condition is displayed on the display device. A measurer selects diffraction conditions in which resolution is higher from among the diffraction conditions, and selects a diffraction condition in which an intensity is obtained from among the selected diffraction conditions.

8 Claims, 6 Drawing Sheets

(51) Int. Cl.
*G01J 3/02* (2006.01)
*G01J 3/04* (2006.01)

(56) References Cited

U.S. PATENT DOCUMENTS

| | | | |
|---|---|---|---|
| 2015/0070695 A1* | 3/2015 | Minato | G01J 3/18 356/319 |
| 2015/0276484 A1* | 10/2015 | Matsuzawa | G01J 3/443 356/316 |

* cited by examiner

| ELEMENT | WAVELENGTH (nm) | FIRST DIFFRACTION GRATING | INTENSITY RATIO (SECOND DIFFRACTION GRATING/FIRST DIFFRACTION GRATING) SECOND DIFFRACTION GRATING | | |
|---|---|---|---|---|---|
| | | | 1ST | 2ND | 3RD |
| Hg | 194.170 | 1 | 0.21 | 0.35 | 1.13 |
| Mn | 257.610 | 1 | 0.45 | 1.5 | 0.24 |
| Hg | 296.728 | 1 | 0.69 | 2.1 | 0.02 |
| Hg | 313.180 | 1 | 1.2 | 2.37 | 0.02 |
| Hg | 365.015 | 1 | 4.69 | 2.9 | |
| Hg | 404.660 | 1 | 13.37 | 3.5 | |
| Hg | 435.835 | 1 | 65.11 | 6.73 | |

| ELEMENT | WAVELENGTH (nm) | RESOLUTION (pm) | | | |
|---|---|---|---|---|---|
| | | FIRST DIFFRACTION GRATING | SECOND DIFFRACTION GRATING | | |
| | | | 1ST | 2ND | 3RD |
| Hg | 194.170 | 3.86 | 8.38 | 5.29 | 2.93 |
| Mn | 257.610 | 3.28 | 9.18 | 4.10 | 2.66 |
| Hg | 296.728 | 2.95 | 9.00 | 3.48 | 2.51 |
| Hg | 313.180 | 2.84 | 8.80 | 3.49 | 2.39 |
| Hg | 365.015 | 2.71 | 8.37 | 2.95 | |
| Hg | 404.660 | 2.52 | 7.26 | 2.70 | |
| Hg | 435.835 | 2.37 | 6.19 | 2.30 | |

FIG. 5

| OPTION | CONDITION | ORDER | RESOLUTION (pm) | INTENSITY RATIO |
|---|---|---|---|---|
| A | FIRST DIFFRACTION GRATING | 1 | 3.28 | 1.00 |
| B | SECOND DIFFRACTION GRATING | 1 | 9.18 | 0.45 |
| C | SECOND DIFFRACTION GRATING | 2 | 4.10 | 1.50 |
| D | SECOND DIFFRACTION GRATING | 3 | 2.66 | 0.24 |

FIG. 6

| OPTION | CONDITION | ORDER/SLIT | RESOLUTION (pm) | INTENSITY RATIO |
|---|---|---|---|---|
| A | SECOND DIFFRACTION GRATING | 1/FIRST SLIT | 9.18 | 0.45 |
| B | SECOND DIFFRACTION GRATING | 1/SECOND SLIT | 18.37 | 2.25 |
| C | SECOND DIFFRACTION GRATING | 2/FIRST SLIT | 4.10 | 1.50 |
| D | SECOND DIFFRACTION GRATING | 2/SECOND SLIT | 8.20 | 7.50 |
| E | SECOND DIFFRACTION GRATING | 3/FIRST SLIT | 2.66 | 0.24 |
| F | SECOND DIFFRACTION GRATING | 3/SECOND SLIT | 5.31 | 1.20 |

ICP EMISSION SPECTROPHOTOMETER

This application claims priority from Japanese Patent Application No. 2017-054491 filed on Mar. 21, 2017, the entire subject-matter of which is incorporated herein by reference.

TECHNICAL FIELD

The present disclosure relates to a sequential ICP emission spectrophotometer.

BACKGROUND ART

There are techniques of displaying conditions or a calculation amount for analysis on a display device (display unit) of a computer (for example, see JP-UM-A-63-63755 and JP-A-2010-169412).

JP-UM-A-63-63755 discloses an ICP emission spectrophotometer in which a periodic table of elements, or a wavelength or information of a generated spectral line for analysis of any element can be read when analysis procedures are programmed on a computer, and analysis conditions can be input along with reliable information. JP-A-2010-169412 discloses an ICP emission spectrophotometer in which information regarding spectral interference of an interference element on another element is added to a basic database including information regarding a spectral line for each of various target elements, an interference amount of an interference element on a spectral line of a target element is calculated, and an interference amount can be calculated on the basis of the optimized basic database.

SUMMARY

One illustrative aspect of the disclosure may provide an ICP emission spectrophotometer comprising: an inductively coupled plasma device configured to atomize or ionize an analysis target element with inductively coupled plasma to produce an atomic emission light; a spectroscope comprising: an incidence side slit provided on an incidence window to which the atomic emission light is incident; a diffraction grating diffracting the incident atomic emission light; an emission side slit provided on an emission window from which emitted light is emitted, the emitted light being diffracted light of atomic emission light diffracted by the diffraction grating; and a detector configured to detect the emitted light emitted from the emission side slit; and a display device configured to display a diffraction condition for the atomic emission light in the spectroscope, wherein the diffraction condition is given in a form in which combinations are comparable with each other, each of the combinations including a candidate diffraction grating and at least an intensity and a resolution of the emitted light for a specific diffraction order of the candidate diffraction grating.

In the ICP emission spectrophotometer, the diffraction grating may comprise at least a first diffraction grating having a first grating constant and a second diffraction grating having a second grating constant, the second grating constant being different from the first grating constant, and the diffraction condition may include: an intensity and a resolution of the emitted light for a predetermined diffraction order of the first diffraction grating; and an intensity and a resolution of the emitted light for a predetermined diffraction order of the second diffraction grating.

In the ICP emission spectrophotometer, the first diffraction grating may have one diffraction order, and the second diffraction grating may have a plurality of diffraction orders, and the first grating constant may be smaller than the second grating constant.

In the ICP emission spectrophotometer, the diffraction condition may be given in a form of a comparison table in which combinations are listed to be comparable with each other, each of the combinations including each candidate diffraction grating and at least an intensity and a resolution of the emitted light for a specific diffraction order of the each candidate diffraction grating.

In the ICP emission spectrophotometer, the diffraction condition may further include at least one of a slit width of the incidence side slit and a slit width of the emission side slit.

The ICP emission spectrophotometer of the present disclosure displays a diffraction condition in a form in which an intensity and a resolution of emitted light for the type of diffraction grating and the order of the diffraction grating are comparable on a display device, and thus even a beginner can easily select a combination of a diffraction grating, a diffraction order, and the like which are optimum for measurement by referring the diffraction condition. Even a measurer with little experience can set an appropriate condition while viewing a displayed diffraction condition, and thus it is possible to increase effectiveness of the ICP emission spectrophotometer.

BRIEF DESCRIPTION OF THE DRAWINGS

FIGS. 3A and 3B illustrate an example of wavelength dependency of a diffraction intensity of the diffraction grating according to the present disclosure, in which FIG. 3A is a table, and FIG. 3B is a graph;

FIGS. 4A and 4B illustrate an example of wavelength dependency of a resolution of the diffraction grating according to the present disclosure, in which FIG. 4A is a table, and FIG. 4B is a graph;

FIG. 5 is a table illustrating an example of a first embodiment of a diffraction condition according to the present disclosure;

FIG. 6 is a table illustrating an example of a second embodiment of a diffraction condition according to the present disclosure.

DETAILED DESCRIPTION

In the above-described related-art technology, information regarding a wavelength of a spectral line or an interference amount is displayed, but a diffraction condition which tends to depend on experience is not disclosed. Setting of a diffraction condition is determined on the basis of selection of a wavelength of each measurement element, a diffraction order, and a slit width, but a beginner has to rely on advice of an experienced person. However, there is the need to easily set a diffraction condition from the viewpoint of effective use of a device, but a technique for easy setting is not disclosed in the related art.

Therefore, illustrative aspects of the present disclosure provide an ICP emission spectrophotometer in which measurement conditions including a diffraction condition can be easily set.

Hereinafter, preferred embodiments of an ICP emission spectrophotometer according to the present disclosure will be described in detail with reference to FIGS. 1 to 7.

Figure 1:
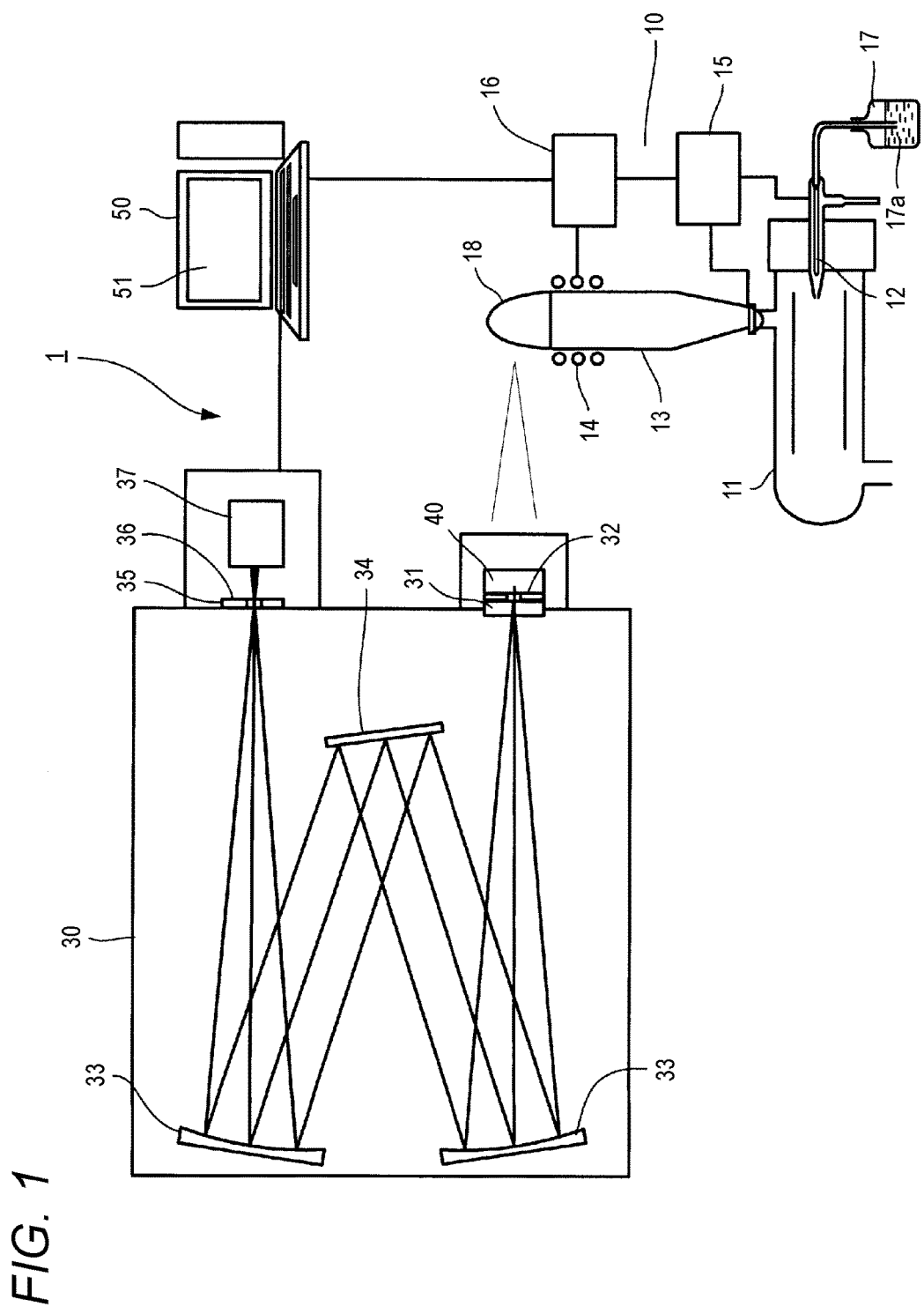
FIG. 1 is a configuration block diagram illustrating an example of an ICP emission spectrophotometer according to the present disclosure.
Figure 2:
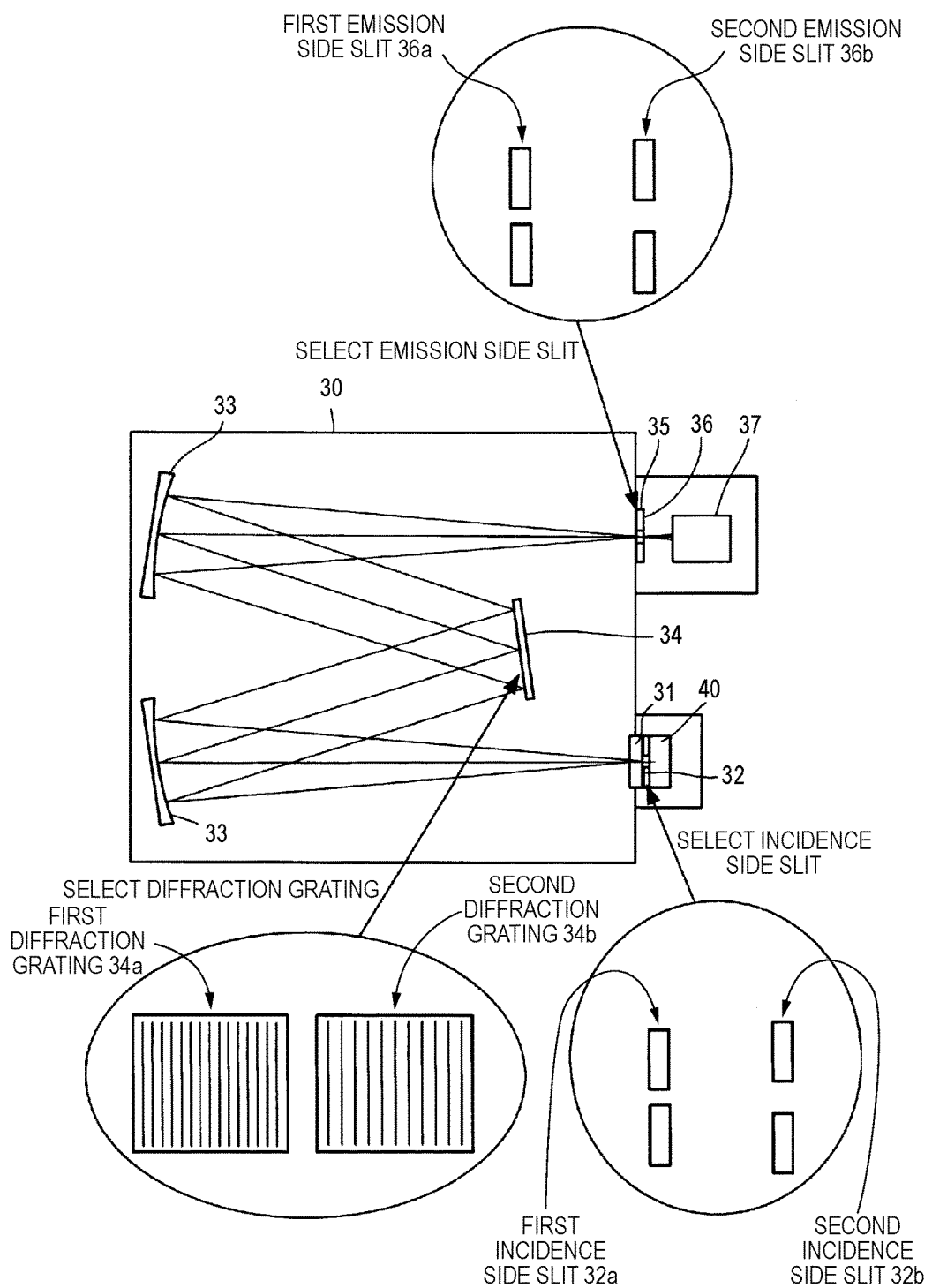
FIG. 2 is a schematic diagram illustrating selection of a diffraction grating and a slit according to the present disclosure.

FIG. 1 is a configuration block diagram illustrating an example of an ICP emission spectrophotometer according to the present disclosure. FIG. 2 is a schematic diagram illustrating selection of a diffraction grating and a slit. With reference to FIGS. 1 and 2, a detailed description will be made of a configuration of the ICP emission spectrophotometer of the present embodiment.

An ICP emission spectrophotometer 1 of the present embodiment includes an inductively coupled plasma device 10, a spectroscope 30, and a computer 50. The inductively coupled plasma device 10 is approximately formed of a spray chamber 11, a nebulizer 12, a plasma torch 13, a high frequency coil 14, a gas control unit 15, and a high frequency power source 16. An optical fiber through which atomic emission light from inductively coupled plasma 18 are guided may be disposed between the inductively coupled plasma 18 and the spectroscope 30, and may be connected to an attachment member 40 of the spectroscope 30.

The spectroscope 30 includes an incidence window 31, an incidence side slit 32 provided on the incidence window 31, concave mirrors 33, a diffraction grating 34, an emission window 35, an emission side slit 36 provided on the emission window 35, and a detector 37. Measurement conditions (diffraction condition) and a measurement result are displayed on a display device 51 of the computer 50.

An argon gas controlled by the gas control unit 15 is guided to the plasma torch 13. A high frequency current flows from the high frequency power source 16 to the high frequency coil 14, and thus the argon gas generates the inductively coupled plasma 18 (hereinafter, referred to as plasma) upward of the plasma torch 13. On the other hand, a carrier gas (argon gas) supplied into the nebulizer 12 is ejected from a tip end of the nebulizer 12 in the spray chamber 11, a solution sample 17a in a sample container 17 can be sucked up due to negative pressure suction of the carrier gas, and thus the sample is sprayed from the tip end of the nebulizer 12. The sprayed solution sample 17a is made to have uniformized particles and a stabilized airflow in the spray chamber 11, and is controlled by the gas control unit 15 so as to be guided to the plasma torch 13. Sample molecules (or atoms) of the solution sample 17a are heated and excited in the plasma 18 so as to emit light.

An atomic emission light produced by atomizing or ionizing an analysis target element of the solution sample 17a with the plasma 18 is incident to the spectroscope 30 from the incidence side slit 32 via the incidence window 31. The atomic emission light is dispersed by the concave mirror 33 or the diffraction grating 34 in the spectroscope 30, and is converted into diffracted light through diffraction in the diffraction grating 34, so as to be emitted as emission light from the emission side slit 36 of the emission window 35, and is then detected by the detector 37. The atomic emission light which is dispersed and detected by the spectroscope 30 is analyzed through data analysis in the computer 50 or the like. Qualitative analysis of an element (for example, a trace impurity element) contained in the solution sample 17a is performed on the basis of a wavelength of the atomic emission light (spectral line), and quantitative analysis of the element is performed on the basis of an intensity of the atomic emission light (spectral line).

With reference to FIG. 2, a description will be made of a case where there are a plurality of incidence side slits 32, emission side slits 36, and diffraction gratings 34.

Plasma light to be measured is guided to the incidence side slit 32 via the incidence window 31. In order to switch between measurement intensities or resolutions, as illustrated in FIG. 2, the incidence side slit 32 may include a plurality of slits with different slit widths, for example, a first incidence side slit 32a and a second incidence side slit 32b, and the first incidence side slit 32a and the second incidence side slit 32b may be selected.

The light to be measured having passed through the incidence side slit 32 is guided to the diffraction grating 34 via the concave mirror 33. In the diffraction grating 34, a rotation angle of the diffraction grating 34 may be set according to a condition for diffracting a wavelength to be measured. The diffraction grating 34 may include a plurality of diffraction gratings having different grating constants, for example, a first diffraction grating 34a and a second diffraction grating 34b, and the first diffraction grating 34a and the second diffraction grating 34b may be selected.

The diffracted light is collected at the emission side slit 36 via another concave mirror 33. In order to switch between measurement intensities or resolutions, the emission side slit 36 may include a plurality of slits having different slit widths, for example, a first emission side slit 36a and a second emission side slit 36b, and the first emission side slit 36a and the second emission side slit 36b may be selected.

Figures 3A, 3B:
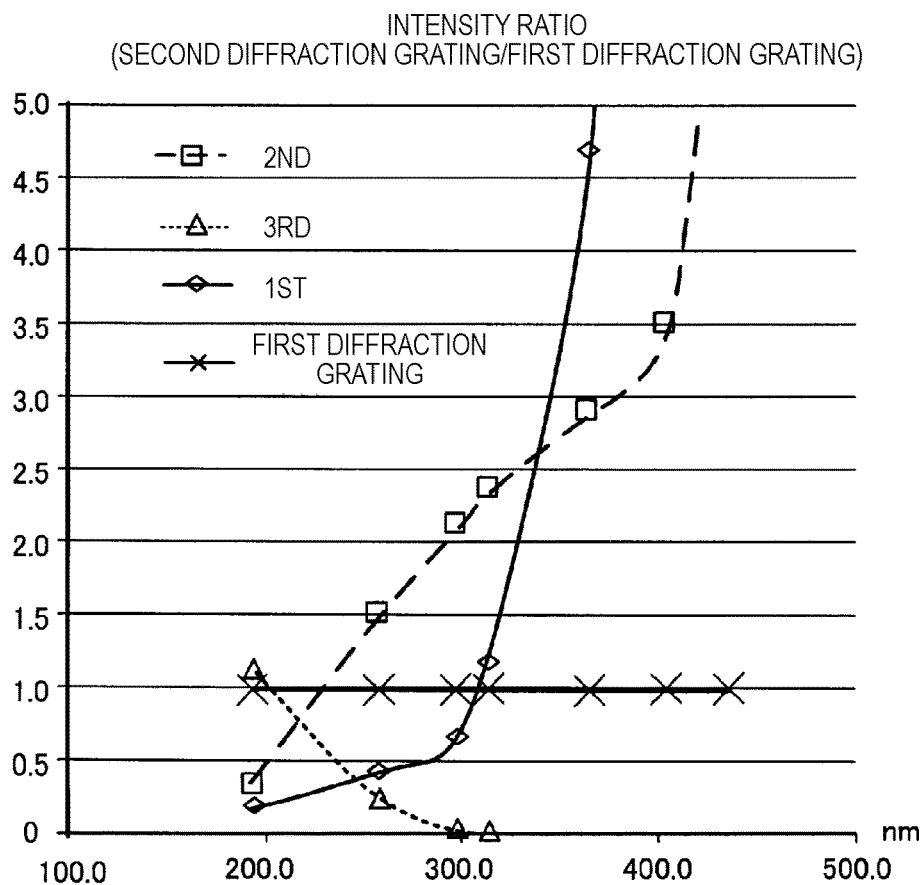

With reference to FIGS. 3A and 3B, a description will be made of an example of wavelength dependency of diffraction intensity of the diffraction grating 34. A graph of FIG. 3B illustrates intensity ratio-wavelength dependency for each diffraction condition. A high resolution diffraction grating is selected as the first diffraction grating 34a, and a long wavelength diffraction grating is selected as the second diffraction grating 34b. Mercury (Hg) and manganese (Mn) shown in a table of FIG. 3A are elements with peak wavelengths, and correspond to those in the graph.

The first diffraction grating 34a which is a high resolution diffraction grating has a large number of grooves per mm, and thus normally serves as a holographic diffraction grating, and only 1 is used as a diffraction order. Since the number of grooves is large, a resolution is favorable, but a long wavelength cannot be diffracted. Therefore, a blazed diffraction grating, in which the number of groove is small and thus diffraction intensity can be obtained, is selected as the second diffraction grating 34b which is a long wavelength diffraction grating.

In the selection, it can be seen from the graph that diffraction intensity of 1st order light increases on a long wavelength side in the long wavelength diffraction grating (second diffraction grating 34b) more than in the high resolution diffraction grating (first diffraction grating 34a) on the basis of the intensity ratio-wavelength dependency of measurement intensity. On the other hand, it can be seen that the intensity of 2nd order light increases toward a short wavelength side (e.g., medium wavelength side), and the intensity of 3rd order light increases toward a further short wavelength side. It can be seen from the above description that a condition for obtaining diffraction intensity is changed depending on a wavelength.

Figures 4A, 4B:
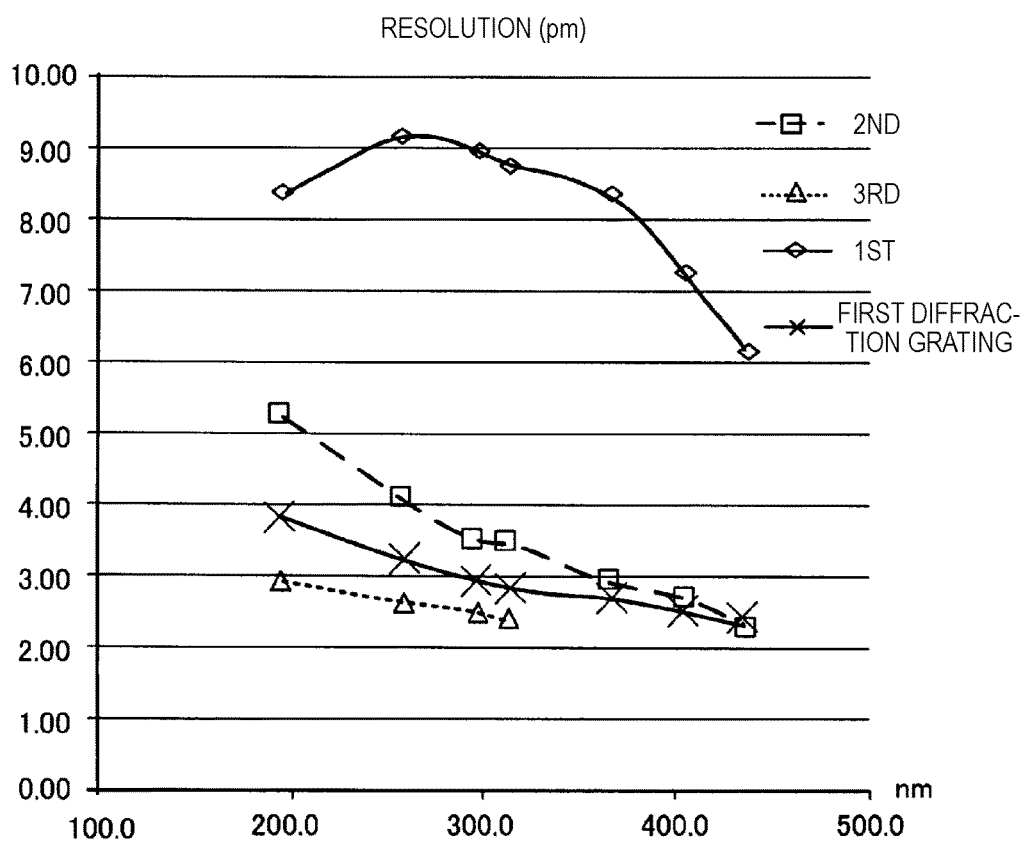

With reference to FIG. 4, a description will be made of an example of wavelength dependency of a resolution of the diffraction grating 34. A resolution on a longitudinal axis in FIG. 4B is illustrated in a graph according to a width of a wavelength profile, and the graph indicates that the resolution becomes lower upward of the longitudinal axis due to an increase in the profile width. In other words, it can be seen that the 1st order light of which diffraction intensity can be obtained in FIGS. 3A and 3B has a low resolution. It can be seen from FIGS. 3 and 4 that diffraction intensity and a resolution have a trade-off relationship, the trade-off relationship differs in 1st order light, 2nd order light, and 3rd order light.

The trade-off relationship makes it hard to set a diffraction condition. Therefore, setting of the diffraction condition tends to depend on experience of an experienced person. Therefore, when qualitative analysis and quantitative analysis of an element are performed by using the ICP emission spectrophotometer 1 of the present embodiment, first, a specific peak of a sample to be tested is correlated with the type of basic diffraction grating and the diffraction order of diffracted light in the diffraction condition, and an intensity-resolution comparison table between diffraction conditions is displayed on the display device 51 in advance. Therefore, even a person with little experience can set appropriate conditions while viewing the displayed intensity-resolution comparison table.

An appropriate diffraction condition may be determined on the basis of an intensity of diffracted light (FIGS. 3A and 3B) and a resolution (FIGS. 4A and 4B). However, a higher intensity is preferable, but wavelength dependency thereof differs for each type of diffraction grating and each diffraction order. As illustrated in the graph of FIG. 3B, in a case where the intensity of diffracted light obtained from the high resolution first diffraction grating 34a is set to 1 over all wavelengths, wavelength dependency of the intensity of diffracted light obtained from the long wavelength second diffraction grating 34b differs depending on the order thereof as indicated by the graph. In terms of the intensity, the intensity of 1st order light is favorable (high) in a long wavelength, the intensity of 2nd order light is favorable (high) in a medium wavelength, and the intensity of 3rd order light is favorable (high) in a short wavelength. On the other hand, from the graph of FIG. 4B, in terms of the resolution, the resolution becomes lower in the order of the 3rd order light, the 2nd order light, and the 1st order light in the entire wavelength region (the resolution becomes decreased as the value of the vertical axis increases in the graph).

As mentioned above, a change in the intensity or the resolution shows different behaviors with respect to a change in a combination of the type of diffraction grating 34 and the diffraction order, and thus a table similar to a table illustrated in FIG. 5 is displayed on the display device 51 in the present embodiment such that an appropriate combination can be selected for each peak wavelength of a measurement sample. Even a beginner as a measurer can select an appropriate combination while viewing the table.

As an example of an option of the diffraction grating 34, for example, a high resolution diffraction grating having 4320 grooves per mm is selected as the first diffraction grating 34a, and, for example, a long wavelength diffraction grating having 1800 grooves per mm is selected as the second diffraction grating 34b. For the first diffraction grating 34a, only a diffraction order of 1 can be used, and, for the second diffraction grating 34b, diffraction orders of not only 1 but also 2 (corresponding to 3600 grooves), 3 (corresponding to 5400 grooves), . . . can be used.

In other words, for the high resolution diffraction grating (first diffraction grating 34a), only 1 can be used as the diffraction order, a grating constant is small, and a number density of grooves is large. On the other hand, for the long wavelength diffraction grating (second diffraction grating 34b), 1 or more can be used as the diffraction order, a grating constant is large, and a number density of grooves is small. In the present embodiment, the first diffraction grating 34a has only a single diffraction order, the second diffraction grating 34b has a plurality of diffraction orders, and a grating constant of the first diffraction grating 34a is smaller than that of the second diffraction grating 34b.

With reference to a table of FIG. 5, a description will be made of an example of a first embodiment of a diffraction condition. The table of FIG. 5 illustrates diffraction conditions including four options A, B, C and D as options which can be selected by a measurer. Each option is given as a combination (corresponding to one row of the table) including at least an intensity and a resolution of emitted light for a diffraction grating and a specific diffraction order (1 to 3) of the diffraction grating. The diffraction conditions in the table of FIG. 5 are given in the form of a comparison table in which the respective options, that is, the respective combinations can be compared with each by the measurer, and thus the measurer can easily compare the respective combinations with each other. In this example, the measurer may select any one of two types of diffraction gratings such as the first diffraction grating and the second diffraction grating as a diffraction condition, and may select a diffraction order of the second diffraction grating as a diffraction condition.

An example of a measurement target is manganese (Mn) with a wavelength of 257.610 nm. A large number of measurement elements interfere with coexisting elements due to emission light, and thus a required resolution is selected on the basis of an interfering intensity of an element interfering with the measurement element such that the measurement target hardly interferes. If a spectrum of the interfering element present near Mn (257.610 nm) of the present embodiment is close to that of Mn, diffraction conditions satisfying a resolution condition are extracted, and a diffraction condition in which an intensity can be obtained is selected from among the diffraction conditions.

Case 1: In a case where a required resolution is 3 pm on the basis of a relationship with an interference line, it can be seen from the table of FIG. 5 that a resolution of 2.66 pm satisfies the required resolution of 3 pm or less, and the option D including said resolution and the diffraction order of 3 of the second diffraction grating 34b is selected as a diffraction condition, though a measurement intensity to be obtained from the option D is the minimum among the displayed diffraction conditions.

Case 2: In a case where a required resolution is 4 pm on the basis of a relationship with an interference line, it can be seen from the table of FIG. 5 that options including resolution of 2.66 pm or 3.28 pm may be selected as satisfying the required resolution of 4 pm or less, but the option A including the resolution of 3.28 pm and the first diffraction grating 34a is selected as a diffraction condition, as the option A corresponds to a higher intensity ratio. A measurement intensity to be obtained in Case 2 is about four times higher than in Case 1.

Case 3: In a case where a required resolution is 5 pm on the basis of a relationship with an interference line, it can be seen from the table of FIG. 5 that options including resolution of 3.28 pm, 4.10 pm, or 2.66 pm may be selected as satisfying the required resolution of 5 pm or less, but the option C including the resolution of 4.10 pm and the diffraction order of 2 at the second diffraction grating 34b is selected as a diffraction condition, as the option C corresponds to a higher intensity ratio. A measurement intensity to be obtained in Case 3 is about six times higher than in Case 1.

Case 4: In a case where there is no interference, the option C including the diffraction order of 2 at the second diffraction grating 34b is selected as a diffraction condition. In Case 4, there is no interference line which interferes near a specific peak, a resolution may be low, and an intensity is prioritized.

With reference to a table of FIG. 6, a description will be made of an example of a second embodiment of a diffraction condition. The table of FIG. 6 illustrates diffraction conditions including six options A, B, C, D, E and F as options which can be selected by a measurer. Each option is given as a combination (corresponding to one row of the table) including at least an intensity and a resolution of emitted light for a diffraction grating (restricted to the second diffraction grating in this example), a specific diffraction order (1 to 3) of the diffraction grating, and a selected slit. The diffraction conditions in the table of FIG. 6 are given in the form of a comparison table in which the respective options, that is, the respective combinations can be compared with each by the measurer, and thus the measurer can easily compare the respective combinations with each other. In this example, only one type of diffraction grating (only the second diffraction grating) is given unlike in FIG. 5 in which two types of diffraction gratings (the first diffraction grating and the second diffraction grating) can be selected, and a diffraction order and a slit (an incidence side slit or an emission side slit) may be selected independently as a diffraction condition.

An example of a measurement target is manganese (Mn) with a wavelength of 257.610 nm in the same manner as in the first embodiment. This example is an example in a state in which the second diffraction grating 34b is selected. In the table, "first slit" is a setting condition in which the first incidence side slit 32a is used as an incidence side slit, and the first emission side slit 36a is used as an emission side slit, and "second slit" is a setting condition in which the second incidence side slit 32b is used as an incidence side slit, and the second emission side slit 36b is used as an emission side slit. Here, a slit width of the second incidence side slit 32b is larger than that of the first incidence side slit 32a. Similarly, a slit width of the second emission side slit 36b is larger than that of the first emission side slit 36a.

Case 1: In a case where a required resolution is 3 pm on the basis of a relationship with an interference line, it can be seen from the table of FIG. 6 that a resolution of 2.66 pm satisfies the required resolution of 3 pm or less, and the option E including said resolution and the diffraction order of 3/first slit (in which related the first incidence side slit 32a and the first emission side slit 36a are used) is selected as a diffraction condition, though a measurement intensity to be obtained from the option E is the minimum among the displayed diffraction conditions.

Case 2: In a case where a required resolution is 4 pm on the basis of a relationship with an interference line, it can be seen from the table of FIG. 6 that a resolution of 2.66 pm satisfies the required resolution of 4 pm or less, and the option E including said resolution and the diffraction order of 3/first slit (in which the first incidence side slit 32a and the first emission side slit 36a are used) is selected as a diffraction condition in the same manner as in Case 1.

Case 3: In a case where a required resolution is 5 pm on the basis of a relationship with an interference line, it can be seen from the table of FIG. 6 that options including resolutions of 2.66 pm or 4.10 pm may be selected as satisfying the required resolution of 5 pm or less, but the option C including the resolution of 4.10 pm and the diffraction order of 2/first slit (in which the first incidence side slit 32a and the first emission side slit 36a are used) is selected as a diffraction condition, as the option C corresponds to a higher intensity ratio. A measurement intensity to be obtained in Case 3 is about six times higher than in Case 1.

Case 4: In a case where there is no interference, the option D including the diffraction order of 2/second slit (in which the second incidence side slit 32b and the second emission side slit 36b are used) is selected as a diffraction condition. In Case 4, there is no interference line which interferes near a specific peak, a resolution may be low, and an intensity is prioritized.

The diffraction condition in the second embodiment includes the slit width of the incidence side slit 32 and the slit width of the emission side slit 36, but the diffraction condition may include one or both of the slit widths thereof. The incidence side slit width and the emission side slit width may be separately selected.

Figure 7:
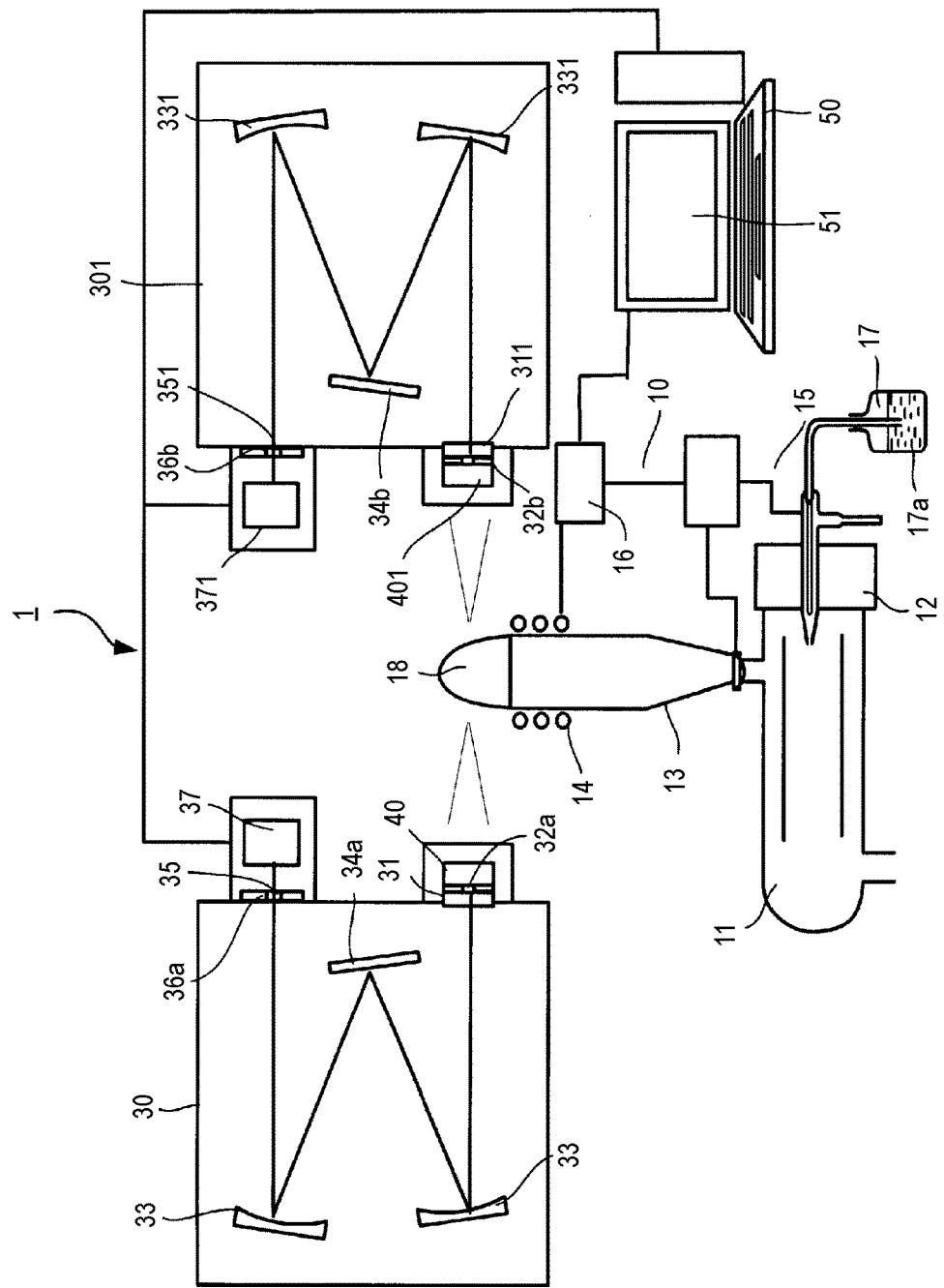
FIG. 7 is a configuration block diagram illustrating an example of a third embodiment of a diffraction condition according to the present disclosure.

FIG. 7 illustrates an example of an ICP emission spectrophotometer 1 used in a third embodiment of a diffraction condition. The ICP emission spectrophotometer 1 includes the spectroscope 30 (a first spectroscope 30 and a second spectroscope 301) on each side of the plasma torch 13. A diffraction condition will be described with reference to FIGS. 7 and 5.

An atomic emission light from the plasma 18 is guided to the first spectroscope 30 and the second spectroscope 301 via incidence windows 31 and 311. The first spectroscope 30 is provided with a first incidence side slit 32a, a first diffraction grating 34a, and a first emission side slit 36a. In the same manner as the first spectroscope 30, the second spectroscope 301 is provided with the incidence window 311, a second incidence side slit 32b (having the same configuration as that of the first incidence side slit 32a in the present embodiment), concave mirrors 331, a second diffraction grating 34b, an emission window 351, a second emission side slit 36b (having the same configuration as that of the first emission side slit 36a in the present embodiment), and a detector 371.

Case 1: In a case where a required resolution is 3 pm on the basis of a relationship with an interference line, it can be seen from the table of FIG. 5 that a resolution of 2.66 pm satisfies the required resolution of 3 pm or less, and the option D including said resolution and the diffraction order of 3 of the second diffraction grating 34b is selected as a diffraction condition, though a measurement intensity to be obtained from the option D is the minimum (0.24) among the displayed diffraction conditions.

Case 2: In a case where a required resolution is 4 pm on the basis of a relationship with an interference line, it can be seen from the table of FIG. 5 that options including resolution of 2.66 pm or 3.28 pm may be selected as satisfying the required resolution of 4 pm or less, but the option A including the resolution of 3.28 pm and the first diffraction grating 34a is selected as a diffraction condition, as the option A corresponds to a higher intensity ratio. A measurement intensity to be obtained in Case 2 is about four times higher than in Case 1.

Case 3: In a case where a required resolution is 5 pm on the basis of a relationship with an interference line, it can be seen from the table of FIG. 5 that options including resolution of 3.28 pm, 4.10 pm, or 2.66 pm may be selected as satisfying the required resolution of 5 pm or less, but the option C including the resolution of 4.10 pm and the diffraction order of 2 at the second diffraction grating 34b is selected as a diffraction condition, as the option C corresponds to a higher intensity ratio. A measurement intensity to be obtained in Case 3 is about six times higher than in Case 1.

Case 4: In a case where there is no interference, the option C including the diffraction order of 2 at the second diffraction grating 34b is selected as a diffraction condition. In Case 4, there is no interference line which interferes near a specific peak, a resolution may be low, and an intensity is prioritized.

As mentioned above, a diffraction condition includes at least an intensity and a resolution of emitted light for a combination of the diffraction grating 34 and a diffraction order of the diffraction grating 34. In other words, a measurement intensity-resolution comparison table between measurement conditions including diffraction conditions which are selectable are displayed on the display device 51. Since the diffraction conditions are displayed on the display device 51, even a beginner can easily select a diffraction condition, it is not necessary that measurement targets are measured for each measurement wavelength under all diffraction conditions for the spectroscope 30, and a diffraction condition is set on the basis of a measurement result.

In the embodiments, a diffraction condition is given in the form of a comparison table in which respective combinations (options) can be compared with each other. However, a display form of a diffraction condition is not limited to the form of a comparison table, and various display forms (figures, moving images, or the like) can be employed as long as a measurer can select each combination (option) through comparison.

The first diffraction grating 34a and the second diffraction grating 34b have been described with respect to the diffraction grating 34, but three or more diffraction gratings may be provided, and each thereof can cope with one or a plurality of diffraction orders. An intensity and a resolution are displayed for each combination.

For better understanding of description, "first" and "second" such as the first diffraction grating and the second diffraction grating have been used, but a positional relationship, a type, a number, and the like are not limited.

The present disclosure is not limited to the above-described embodiments, and may be modified or altered as appropriate. Any materials, shapes, dimensions, numerical values, forms, number, arrangement locations, and the like of the respective constituent elements in the above-described embodiments may be employed and are not limited as long as the present disclosure can be achieved.

The ICP emission spectrophotometer according to the present disclosure enables even a beginner to select a combination of a diffraction grating and a diffraction order or a combination of a diffraction order and a slit, which is the optimum for measurement, and is thus applicable to a field in which effectiveness of a device is desired to be increased.

What is claimed is:

1. An ICP emission spectrophotometer comprising:
    an inductively coupled plasma device configured to atomize or ionize an analysis target element with inductively coupled plasma to produce an atomic emission light;
    a spectroscope comprising:
        an incidence side slit provided on an incidence window to which the atomic emission light is incident;
        a diffraction grating diffracting the incident atomic emission light;
        an emission side slit provided on an emission window from which emitted light is emitted, the emitted light being diffracted light of atomic emission light diffracted by the diffraction grating; and
        a detector configured to detect the emitted light emitted from the emission side slit; and
    a display device configured to display a diffraction condition including a diffraction order for the atomic emission light in the spectroscope,
    wherein the diffraction condition is given in a form in which combinations are comparable with each other, each of the combinations including a candidate diffraction grating and at least an intensity and a resolution of the emitted light for a specific diffraction order of the candidate diffraction grating.

2. The ICP emission spectrophotometer according to claim 1,
    wherein the diffraction grating comprises at least a first diffraction grating having a first grating constant and a second diffraction grating having a second grating constant, the second grating constant being different from the first grating constant, and
    wherein the diffraction condition includes:
        an intensity and a resolution of the emitted light for a predetermined diffraction order of the first diffraction grating; and
        an intensity and a resolution of the emitted light for a predetermined diffraction order of the second diffraction grating.

3. The ICP emission spectrophotometer according to claim 2,
    wherein the first diffraction grating has one diffraction order, and the second diffraction grating has a plurality of diffraction orders, and
    wherein the first grating constant is smaller than the second grating constant.

4. The ICP emission spectrophotometer according to claim 1,
    wherein the diffraction condition is given in a form of a comparison table in which combinations are listed to be comparable with each other, each of the combinations including each candidate diffraction grating and at least an intensity and a resolution of the emitted light for a specific diffraction order of the each candidate diffraction grating.

5. The ICP emission spectrophotometer according to claim 1, wherein the diffraction condition further includes at least one of a slit width of the incidence side slit and a slit width of the emission side slit.

6. The ICP emission spectrophotometer according to claim 1,
    wherein the incidence side slit is selectable from a plurality of incidence side slits with different slit widths, and
    wherein the emission side slit being selectable from a plurality of emission side slits with different slit widths.

7. The ICP emission spectrophotometer according to claim 6,
    wherein the plurality of incidence side slits with different slit widths includes a first incidence side slit having a first incidence-side slit width and a second incidence side slit having a second incidence-side slit width that is larger than the first incidence-side slit width, and
    wherein the plurality of emission side slits with different slit widths includes a first emission side slit having a first emission-side slit width and a second emission side slit having a second emission-side slit width that is larger than the first emission-side slit width.

8. The ICP emission spectrophotometer according to claim 1,
wherein the incidence side slit is selectable from a plurality of incidence side slits with the same slit direction, and
wherein the emission side slit being selectable from a plurality of emission side slits with the same slit direction.

* * * * *